United States Patent
Harcum et al.

(10) Patent No.: US 6,258,342 B1
(45) Date of Patent: Jul. 10, 2001

(54) PROCESS FOR MAKING TOOTHPASTE USING AGGLOMERATED DISPERSIBLE POLYMERS

(75) Inventors: Weldon Wright Harcum; Jashawant J. Modi, both of New Castle County, DE (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/432,542

(22) Filed: Nov. 3, 1999

(51) Int. Cl.$^7$ ........................................ A61K 7/16
(52) U.S. Cl. ........................ 424/49; 264/117; 264/118
(58) Field of Search .................... 264/117, 118; 424/49–58

(56) References Cited

U.S. PATENT DOCUMENTS

| | | | |
|---|---|---|---|
| Re. 29,634 | * 5/1978 | Robertson et al. | 424/49 |
| 2,662,882 | * 12/1953 | Christianson et al. | 210/209.5 |
| 3,396,034 | * 8/1968 | Blondheim et al. | 99/93 |
| 3,935,306 | * 1/1976 | Roberts et al. | 424/49 |
| 3,955,942 | * 5/1976 | Coroon et al. | 51/295 |
| 4,443,564 | * 4/1984 | Hauschild et al. | 52/105 |
| 4,557,938 | * 12/1985 | Sander et al. | 426/453 |
| 4,696,762 | 9/1987 | Sander et al. | 252/311 |
| 4,735,659 | 4/1988 | Bishop | 106/193 |
| 5,003,060 | 3/1991 | Vinot | 536/114 |
| 5,270,459 | 12/1993 | Shatzman et al. | 536/114 |
| 5,320,847 | 6/1994 | Valentine et al. | 424/439 |
| 5,707,958 | * 1/1998 | Mallari et al. | 510/444 |
| 5,718,969 | 2/1998 | Sewall et al. | 428/304.4 |
| 5,800,755 | * 9/1998 | Withenshaw et al. | 264/117 |
| 5,869,029 | * 2/1999 | Graff-Anderson et al. | 426/52 |
| 5,893,943 | * 4/1999 | Durham et al. | 95/65 |
| 5,932,193 | * 8/1999 | Lopez et al. | 424/52 |
| 5,968,891 | * 10/1999 | Mallari et al. | 510/444 |

* cited by examiner

*Primary Examiner*—Shep K. Rose
(74) *Attorney, Agent, or Firm*—David Edwards

(57) ABSTRACT

An improved process for preparing an oral care composition of mixing at least one dry oral care ingredient and a dry water-soluble or water-swellable polymer, the improvement is by replacing the dry, water-soluble or water-swellable polymer with a particulate water-soluble or water-swellable polymer which has been at least partially agglomerated by treatment with water or an aqueous solution of polymer(s) and drying the agglomerated particles.

28 Claims, No Drawings

PROCESS FOR MAKING TOOTHPASTE USING AGGLOMERATED DISPERSIBLE POLYMERS

FIELD OF THE INVENTION

This invention relates to using a composition of water-soluble or water-swellable polymer agglomerated by treatment with water or an aqueous solution of the polymer and drying for making oral care compositions.

BACKGROUND OF THE INVENTION

Oral care compositions generally refer to dentifrice and dental adhesives. Dentifrice formulations generally contain dentally acceptable abrasive, humectant, water, and water-soluble polymer which serves as a thickener and binder for the ingredients. A variety of other ingredients such as flavors, color, vitamins, antiplaque, anti-tarter, breath freshener, color, sweeteners, preservatives and fluoride are also used at low levels. Glycerol and sorbitol (usually as an aqueous solution) are the most commonly used humectants for dentifrice, and depending on the characteristics desired in the product, polyethylene glycol or propylene glycol may be incorporated as well. Four types of dentifrice are widely produced: 1) cream, 2) transparent or translucent gel, 3) stripes of cream and gel, and 4) dry powders.

The thickeners or binders used for dentifrice are carboxymethyl cellulose (CMC), hydroxyethyl cellulose (HEC), silica, magnesium aluminum silicate, carrageenan, xanthan, guar, alginate, polyacrylic acids, salts of polyacrylic acids, polymers of ethylene oxide, copolymer of ethylene oxide and propylene oxide, processed euchemia seaweed (PES), starch, starch derivatives, pectin, and agar.

In the manufacturing process for dentifrice, incorporation of a dry water-soluble binder polymer into the composition often presents difficulties because of the tendency for lump formation when the dry polymers are added to and dispersed in aqueous systems. This increases the time required to obtain uniform hydration or uniform dispersion of the binder polymer. And sometimes, portions of the polymer could remain in dentifrice in partially hydrated gel form. This can not only affect dentifrice shelf stability and rheology but would also make dentifrice aesthetically unappealing. A re-occurring problem in the dentifrice industry is to make a polymer that is universally dispersible regardless of the environment in which it is to be used. Making a polymer dispersible based on a particular formulation has been done prior to the present invention but that makes a polymer formulation specific. Consequently, there is a need in the industry for a method of incorporating water-soluble binder polymers into dentifrice formulations universally which lead to dust-free and lump-free products, rapid viscosity development and reduced batch preparation time, and allow convenient handling of the binder.

U.S. Pat. No. 5,869,029 discloses a dentifrice composition using an agglomerated composition of a water-soluble polymer at least partially agglomerated by treatment with at least one polyol. U.S. Pat. No. 3,396,034 discloses a process of converting a hard to disperse particulate cellulose ether material or vegetable gum into a readily dispersible, dust-free particulate material by subjecting fine particles to water spray in an amount sufficient to cause superficial hydration. U.S. Pat. No. 4,557,938 discloses a process for preparing a dispersible agglomerated vegetable gum/carrier particles by dry blending particulate carrier, such as starch and the vegetable gum in a fluid bed dryer. The fluidized vegetable gum and starch particles are sprayed with water to wet the surface of the particles to cause agglomeration. U.S. Pat. No. 3,455,714 discloses the agglomerating of a water-soluble polymer with water-soluble cellulose ether that does not have a tendency to agglomerate when added to water. Japanese Patent No. 93075369 B discloses a method of spraying water onto water-soluble powdery paste under fluidized state and drying the formed granules. The starting powdery paste can be hydroxypropylcellulose or carboxymethylcellulose among other polymers.

None of the above patents discloses the use of water or aqueous polymer agglomerated water-soluble or water-swellable polymer in oral care compositions.

SUMMARY OF THE INVENTION

This invention relates to an improved process for preparing an oral care composition comprising of at least one dry, water-soluble or water-swellable polymer (excluding methylhydroxypropylcellulose alone), the improvement comprising substituting for the dry, water-soluble or water-swellable polymer, a particulate water-soluble or water-swellable polymer which has been at least partially agglomerated by treatment with water alone or an aqueous solution of a water-soluble polymer or polymers and drying. The particulate water-soluble or water-swellable polymer which has been at least partially agglomerated by such treatment with water alone or an aqueous solution of the water-soluble polymer and dried, hydrates in polyhydric alcohol, water, or water-containing solvents substantially faster than the corresponding untreated water-soluble or water-swellable polymer, without the formation of polymer lumps and being dust free.

DETAILED DESCRIPTION OF THE INVENTION

It was surprisingly found that a particulate water-soluble or water-swellable polymer at least partially agglomerated by treatment with water alone or an aqueous solution of the polymer and dried has greater dispersibility without producing dust and formation of polymer lumps in the preparation of oral care compositions. Agglomeration is defined herein as the aggregation of individual particles resulting in an increase in the particle size of the particulate material.

Any natural or synthetic water-soluble or water-swellable polymer may be employed to prepare the composition of this invention. Preferred water-soluble or water-swellable polymers are polysaccharides. Useful polysaccharides may include, but are not limited to, cellulose ethers, guar, guar derivatives, locust bean gum, psyllium, gum arabic, gum ghatti, gum karaya, gum tragacanth, carrageenan, Konjac, agar, alginates, xanthan, scleroglucan, dextran, pectin, starch, starch derivatives, chitin and chitosan.

Preferred polysaccharides are cellulose ethers, carrageenan, guar, guar derivatives and pectin.

Cellulose ethers for use in the invention include hydroxyethyl cellulose (HEC), hydroxypropyl cellulose (HPC), water soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC)(when used in combination with other polymers), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC) and cationic hydrophobically modified hydroxyethyl cellulose (cationic HMHEC). Preferred cellulose ether is carboxymethyl cellulose.

Guar derivatives for use in the invention include carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar) and hydrophobically modified cationic guar (HM cationic guar).

More preferred polysaccharides for use in preparing the oral care compositions of this invention are carboxymethyl cellulose and carrageenan, or mixtures thereof. Most preferred is carboxymethyl cellulose.

The synthetic water-soluble or water-swellable polymers are homo- or copolymer comprising an acrylic acid or acrylic acid salt monomer, homo or copolymer comprising of ethylene oxide or propylene oxide, copolymer of poly (methyl vinyl ether/maleic anhydride), and polyvinylpyrrolidone. The preferred synthetic polymer is a homo- or copolymer comprising an acrylic acid or acrylic acid salt monomer.

Water or an aqueous solution of a polymer(s) is an ideal agglomeration agent because these components are already used in the dentifrice formulations. Hence, these agents are not adding any new or undesirable ingredient that may be undesirable in some formulations. In other words, the polymer is considered neat, i.e., one that does not have any foreign material on it that will affect or limit the final dentifrice product.

The agglomerated compositions may be prepared by spraying particulate polymer with water or an aqueous solution of the polymer or polymers. Commercially available fluidized bed spray units may be employed for the operation.

The agglomerated water soluble or water-swellable polymers of this invention hydrate or dissolve without dusting in water or water-containing solvents or polyhydric alcohol substantially faster than do the corresponding untreated water-soluble or water-swellable polymers. This hydration or dissolving rate is measured using a Haake Visco Tester 501, which measures the amount of torque (force) needed to maintain the rotation of the sensor in the solution at a set speed (400 rpm) as the polymer hydrates and thickening occurs. Hydration time is considered to be the time in minutes it takes to achieve 95% of final viscosity, where the final viscosity is taken as the average of the last 5 minutes viscosity during a one-hour trial.

In this work, hydration in water was determined at 25° C. and/or 55° C. For example, under the above conditions, untreated carboxymethyl cellulose lumped immediately and then required about 15 minutes to reach 95% viscosity; while carboxymethyl cellulose agglomerated by treatment with water or an aqueous solution of CMC quickly dispersed and dissolved in less than five minutes.

An added advantage of these agglomerated polymers is that the agglomeration serves to reduce the amount of dusting that occurs when the untreated polymers are handled. Hence, this reduces both health and safety (e.g., slippery floor or dust inhalation) concerns in the industry.

In the present invention, the process of agglomeration/spray coating can be used for a single polymer coating or blend of polymers. Similarly, spray-coating solution can be of the same polymer as the base polymer or a different polymer or a blend of polymers. The spray coating solution of polymer could be of a solvent such as water (when using CMC, HEC, HPC, guar, pectin, cross-linked acrylic acid polymers), water/ethanol (when using HPC, HPMC, HEC, HP guar), ethanol (when using HPC, cross linked acrylic acid polymers, and HMHEC), polyethylene glycol (when using HPC) propylene glycol (when using HPC, cross-linked acrylic acids) or glycerol (when using HEC), ethanol/polyethylene glycol (when using HPC).

The spray coating solution could also contain ingredients of the oral care formulations, such as a buffering agent, vitamins, whitening agent, color, flavor, abrasive, breath freshener, salts, water, humectants, organic solvents, antimicrobial agent, antiplaque agent, anticavity agent for more uniform distribution of the active ingredients throughout the formulation.

The dentifrice of this invention contains abrasives, humectants, and water-soluble polymers. Humectants are used to retain moisture in dentifrice, particularly at the nozzle end of the tube where the dentifrice can be in prolonged contact with air. The water-soluble polymers serve as thickeners and binders for the ingredients. A variety of other ingredients such as secondary thickener (clay, silica, synthetic polymers), flavors, color, teeth whitening agent, salts (e.g. NaCl, Na benzoate, tetra sodium pyrophosphate), sweeteners, preservatives, detergents, opacifiers, sequestering agents, film formers, vitamins, antimicrobial agent, teeth whitening agents, tartar control agents, plaque control agents and fluoride may also be used at low levels.

The dental abrasives for use in the dentifrice of this invention are typically silica and substantially insoluble inorganic salts. Preferred inorganic salts are dicalcium phosphate, calcium carbonate, dibasic calcium phosphate, tribasic calcium phosphate, calcium sulfate, sodium bicarbonate, insoluble sodium metaphosphate, hydrated aluminum oxide, and magnesium carbonates and phosphates. Silica and silica xerogels are particularly useful for translucent or transparent dentifrice.

Typical humectants for use in the dentifrice of this invention include glycerol, sorbitol, propylene glycol, or mixtures thereof, which are mixed with a suitable humectant vehicle such as water. Other polyhydric alcohols could also be used as humectants such as ribitol, xylitol, mannitol, arabitol, polyethylene glycol, and mixtures thereof.

Dentifrice may contain polyols at a level of from about 0.5 to about 99.5 wt. % based on the total weight of the dentifrice. A preferred level is from about 2 to about 50 wt. %, and a more preferred level is from about 10 to about 30 wt. %.

For preparation of the dentifrice of this invention, the water-soluble or water-swellable polymer which has been agglomerated by treatment with water or aqueous solution of the polymer is stirred with: a) humectant or a mixture of humectants; b) humectant vehicle, most typically water; c)

salts, colorants, and dentifrice actives; d) abrasive; e) surfactants; and f) flavors to obtain a complete dentifrice formulation. In a preferred method of preparation, the agglomerated water-soluble polymer is added directly to the mixture of humectants and humectant vehicle and stirred until the polymer particles are fully dissolved or swollen; then any salts are added, followed by abrasive. The abrasive is added after complete dissolution of the salts. The mixture is stirred until the particles of abrasive are wetted out to form a paste; then the surfactant is added, followed by adding flavors.

In accordance with this invention, the oral care composition can be in the form of a dental adhesive. A dental adhesive is needed mainly when the denture fits poorly to the gums. The function of the dental adhesive is to aid in retaining the denture in the mouth and to provide a cushion (to reduce discomfort) for the gums. Dental adhesives provide an extra degree of security during eating and speaking. The characteristics desired in the dental adhesive, among others, are that it should: be easy to extrude from its container and apply, be stable to microbial growth, be non-toxic, be non-irritant, be odorless, have a non-greasy mouthfeel, and be easy to clean.

Generally, dental adhesives are either in the form of creams or powders. The creams typically include an adhesive (e.g., CMC, copolymer of poly(methyl vinyl ether/maleic anhydride), marketed under the trademark Gantrez by ISP Co. of Wayne, N.J., karaya, polyethylene oxide, gelatin, etc.), a vehicle (e.g., petrolatum, mineral oil, wax, glycerin), a filler (e.g., magnesium oxide), flavor, color, preservative, wetting agent, extrusion aid, and humectant. The powders are almost similar to the creams in the composition except that they do not contain a liquid vehicle. The powder may additionally contain an anticaking agent such as silica.

This invention will be further illustrated by the following examples, which are for illustration purposes only, and are not intended to be limiting thereon. All percentages or parts are by weight unless otherwise indicated.

STANDARD PROCEDURE

For all of the Examples, except where otherwise noted, the polymers were treated in a Glatt Fluid Bed Processor (Model GPCG-5) top spray unit with water or 1% aqueous solutions of the polymer. After the appropriate particle sizes were achieved, the samples were then dried in the Glatt Fluid Bed Processor with an inlet hot air temperature of about 65° C. to below 9% moisture content in the samples and then cooled to ambient temperature. The batch sizes were about 3 kg.

EXAMPLES 1–4

Examples 1–4 demonstrate the testing of carboxymethyl cellulose agglomerated by treatment with water and an aqueous solution of the polymer. Carboxymethyl cellulose was either CMC 9M31XF or CMC 7MXF (available from Hercules Incorporated, Wilmington, Del.).

The agglomerated samples and the untreated controls were evaluated for their dispersibility and hydration/dissolution characteristics in deionized water at 25° C. and/or 55° C. using a Haake VT501 viscometer equipped with a FL 10 sensor. This instrument measures the amount of torque (force) needed to maintain the rotation of the sensor in the solution at the set speed (400 rpm) as the polymer hydrates and thickening occurs. The data are then mathematically converted by computer to viscosity (cps) and % final viscosity.

The hydration time reported in Table 1 and 2 is the time in minutes required to reach 95% of the final viscosity. 100% viscosity is the average viscosity of the last five minutes of a one-hour hydration test.

The data are in Table 1. Comparative Example A and B is presented to show the hydration time for untreated carboxymethyl cellulose.

The data indicate that the hydration time and dust are substantially reduced by agglomeration with water or an aqueous solution of the polymer.

TABLE 1

Agglomerating CMC by Treatment with Aqueous Polymer Solution or Water

| Example No. | Polymer | Treatment | Dispersibility & Dusting | Time to 95% Viscosity @ 25°. min | Time to 95% Viscosity @ 55°. min |
|---|---|---|---|---|---|
| A | CMC 9M31XF | --- | ++Lumping/Dust | 18.4 | 23.4 |
| 1 | CMC 9M31XF | Water | No Lumping No Dust | 1.0 | 0.6 |
| 2 | CMC 9M31XF | CMC 9M31XF Solution | No Lumping No Dust | 0.6 | 0.6 |
| B | CMC 7MXF | -- | ++Lumping/Dust | 24 | 25 |
| 3 | CMC 7MXF | 1% CMC 7MXF Solution | No Lumping No Dust | 0.6 | 0.6 |
| 4 | CMC 7MXF | Water | No Lumping No Dust | 0.8 | 0.6 |

++Many large lumps at start of hydration test, with a few remaining after 60 minuets. CMC 9M31XF: it is anionic carboxymethylcellulose. It has carboxymethyl substitution between 0.8 and 0.95; and has Brookfield viscosity of 1500–3100 cps at 2.0% at 25° C. It is available from Hercules Incorporated, Wilmington, DE.
CMC 7MXF: it is anionic carboxymethylcellulose. It has carboxymethyl substitution between 0.65 and 0.9; and has Brookfield viscosity of 400–800 cps at 2.0% at 25° C. It is available from Hercules Incorporated, Wilmington, DE.

EXAMPLES 5–11

These examples illustrate the agglomeration of Natrosol® 250H, HMHEC 2, and a 1/1 blend of HMHEC 2 and Benecel® MP 843 product by treatment with an aqueous solution of the polymer and by water alone. The data are in Table 2. Comparative Example C, D1, D2, D3, E, and F are presented to show the hydration time for untreated polymer. These Comparative Examples D1, D2, & D3 show that Benecel product alone does not produce an improvement over the prior art. Example 9, however, does show improvement over prior art when the Benecel product is used in combination with another polymer.

The data indicate that the dusting was reduced by agglomeration with water or an aqueous solution of the polymer.

TABLE 2

Agglomerating Of HMHEC 2. Natrosol and Benecel 843 by Treatment with Aqueous Polymer Solution or Water

| Example No. | Polymer | Treatment | Dispersibility & Dusting | Time to 95% Viscosity @ 25° C. [min] | Time to 95% Viscosity @ 55° C. [min] |
|---|---|---|---|---|---|
| C | HMHEC 2 | --- | No Lumping Dust | 5.4 | 2.4 |
| 5 | HMHEC 2 | Water | No Lumping No Dust | 3.8 | 2.7 |
| 6 | HMHEC 2 | HMHEC 2 | No Lumping No Dust | 4.6 | — |
| D1 | Benecel ® MP843 | --- | Lumping/Dust | 200 | — |
| D2 | Benecel ® MP843 | Water | Lumping No Dust | +60 | — |
| D3 | Benecel ® MP843 | Benecel ® MP843 solution | Lumping No Dust | +60 | — |
| E | Natrosol ® 250H | --- | No Lumping Dust | 14 | 9 |
| 7 | Natrosol ® 250H | Water | No Lumping No Dust | 11.6 | 10.4 |
| 8 | Natrosol ® 250H | Natrosol 250H Solution | No Lumping No Dust | 17 | — |
| F | 1:1, Benecel MP843/ HMHEC 2 | --- | A few small Lumps/Dust | 6.4 | — |
| 9 | 1:1, Benecel ® MP843/ HMHEC2 | HMHEC 2 | No Lumping No Dust | 5.5 | — |

HMHEC 2: Hydrophobically modified hydroxyethylcellulose. It is nonionic and has 1.0% aqueous solution viscosity of about 2000 cps at 25° C. It is available from Hercules Incorporated of Wilmington Delaware.
Benecel ® MP843: Hydroxypropyl methylcellulose. It is nonionic and has 2.0% aqueous solution viscosity of about 4,000 cps at 20° C. It is available from Hercules Incorporated of Wilmington, Delaware.
Natrosol ® 250H: hydroxyethyl cellulose. It is nonionic and has 1.0% aqueous viscosity of 1500 to 2500 cps at 25° C. It is available from Hercules Incorporated of Wilmington, Delaware.

EXAMPLES 10 AND 11 AND COMPARATIVE EXAMPLES G

These examples illustrate the dicalcium phosphate abrasive based formulation of dentifrice utilizing carboxymethyl cellulose agglomerated by treatment with water or with polymer solution. The comparative examples demonstrate formulation of control compositions where untreated carboxymethyl cellulose was used.

Examples 10 and 11 illustrate the preparation of dentifrice at room temperature using carboxymethyl cellulose CMC 9M31XF which was agglomerated by treatment with water and with 1.0% solution of CMC 9M31XF, respectively. Comparative example G demonstrates similar formulations where the CMC 9M31XF was untreated. The ingredients and ingredient levels for each formulation are listed in Table 3.

TABLE 3

Dentifrice Formulations. Wt. %

| Ingredient | Example 10 | Example 11 | Comparative Example G |
|---|---|---|---|
| CMC 9M31XF agglomerated with water | 0.90 | | |
| CC 9M31XF agglomerated with 1% solution of 9M31XF | | 0.90 | |
| CMC 9M31XF | | | 0.90 |
| Glycerol | 00.00 | 00.00 | 00.00 |
| Sorbitol (70% aq. sol.) | 35.43 | 35.43 | 35.43 |
| Distilled Water | 8.99 | 8.99 | 8.99 |
| Dicalcium Phosphate, dihydrate | 45.0 | 45.0 | 45.0 |
| Tetrasodium Pyrophosphate | 0.42 | 0.42 | 0.42 |
| Sodium Saccharin | 0.20 | 0.20 | 0.20 |
| Sodium Monofluorophosphate | 0.76 | 0.76 | 0.76 |
| Sodium Benzoate | 0.50 | 0.50 | 0.50 |
| Distilled Water | 6.25 | 6.25 | 6.25 |
| Flavor | 0.55 | 0.55 | 0.55 |
| Sodium Lauryl sulfate | 1.00 | 1.00 | 1.00 |

For the dentifrice formulations (Examples 10, 11 and Comparative Example G), the following procedure was used:

1. Tetra sodium pyrophosphate (0.42 parts), sodium saccharin (0.20 parts) sodium monoflurophosphate (0.76 parts) and sodium benzoate (0.50 parts) were added to 6.25 parts of water with stirring, and heated to about 60° C. to dissolve.

2. The carboxymethyl cellulose (0.9 parts) was added to the sorbitol solution (35.43 parts) in a beaker and stirred for 15 minutes or until adequately dispersed. 8.99 parts of water was then added and the resulting mixture was stirred for 15 to 30 minutes making sure the polymer was completely hydrated (no gels). Then the warm salt solution from Step 1 was added with stirring, which was continued for 15 minutes or until homogeneity (no lumps or gels). The mixture was then transferred to a Ross double planetary mixer.

3. The dicalcium phosphate dihydrate (DCP) (45.00 parts) was added to the mixer and mixing was continued for 10 minutes to completely wet the DCP. The mixer was then opened and the beaters and bowl sides were scraped down. The mixer was then closed; vacuum was applied; and mixing was continued at high speed for 20 minutes or until the mix was smooth.

4. The sodium lauryl sulfate (1.00 parts) was then added and mixing was continued for 5 minutes at low speed without vacuum. Then the flavor (0.55 parts) was added followed by mixing for 2 minutes at low speed. The mixer was then opened and the beaters and bowl sides were scraped down. The mixer was then closed; vacuum was applied; and mixing was continued at medium speed for 15 minutes. The mixer was then shut off; vacuum was broken; and dentifrice was packed out.

EXAMPLES 12 AND COMPARATIVE EXAMPLES H

These examples illustrate the Calcium carbonate abrasive based formulation of dentifrice utilizing carboxymethyl cellulose 9M31XF agglomerated by treatment with water. The comparative examples demonstrate formulation of control compositions where untreated carboxymethyl cellulose was used. The ingredients and ingredient levels for each formulation are listed in Table 4.

TABLE 4

Dentifrice Formulations. Wt. %

| Ingredient | Example 14 | Comparative Example H |
|---|---|---|
| CMC 9M31XF agglomerated with Water | 1.20 | |
| CMC 9M31XF | | 1.20 |
| Glycerol | 0.00 | 00.00 |
| Sorbitol (70% aq. sol.) | 24.00 | 24.00 |
| Distilled Water | 20.6 | 20.6 |
| Calcium Carbonate | 48.00 | 48.00 |
| Sodium Saccharin | 0.20 | 0.20 |
| Sodium Monofluorophosphate | 0.80 | 0.80 |
| Sodium Benzoate | 0.20 | 0.20 |
| Flavor | 0.50 | 0.50 |
| Sodium Lauryl sulfate (33%) | 4.5 | 4.5 |

For the dentifrice formulations (Examples 12 and Comparative Example H), the following procedure was used:

CMC was dispersed in sorbitol and water solution while stirring. The stirring was continued until the CMC was fully hydrated and no gels were observed. The agglomerated CMC dispersed easily without lumping and dusting. The lumping of CMC was observed with the unagglomerated control CMC. Next, sodium saccharin and sodium benzoate were added while mixing. Mixing was continued until no lumps were observed. The slurry was than transferred to Ross double planetary mixer. The abrasive calcium carbonate was added to the mixer and mixed for 10 minutes at low speed to complete wetting of abrasive. The mixer was open to scrape down the stirring blade and walls of the Ross mixer walls. The mixer was closed and mixed at high speed until the dentifrice appeared smooth. The detergent sodium lauryl sulfate and flavor were added and mixed under vacuum at a low speed for 5 minutes and then at a medium speed at 5 minutes. The dentifrice then packed into tubes and glass jars.

EXAMPLE 13

The polymers in this study were evaluated in a model cream denture adhesive formulation, which consisted of 50 wt % of CMC, 45 wt % of petrolatum, and 5 wt % of mineral oil. It should be noted that t he adhesion value is not only affected by the adhesive type and its level, but also by the ratio of the petrolatum to mineral oil.

One hundred-gram batches of denture adhesive were prepared according to the following formula:

| | |
|---|---|
| Petrolatum | 45.0 wt % |
| Mineral Oil | 5.0 wt % |
| CMC 7H3SXF | 50.0 wt % |
| Total | 100.0 wt % |

The petrolatum and mineral oil were weighed into a 250-ml beaker. The beaker was then placed in a circulating oil bath heated to 67° C. The contents were stirred at the lowest speed setting of a Caframo mixer which had two 1 ½" diameter propellers spaced ¼" apart on the shaft. When contents in the beaker were 65oC, the polymer was added slowly while adjusting the mixer speed to maintain a vortex in the mixture. Mixing was continued for one hour.

The dispersible CMC was free flowing and dust free when added to the mineral oil/petrolatum mixture in the beaker.

Artificial saliva was prepared from artificial saliva concentrate having the following composition:

| | |
|---|---|
| Potassium thiocyanate | 2.00 |
| Potassium chloride | 14.00 |
| Sodium phosphate, dibasic, 7-hydrate | 2.00 |
| Sodium phosphate, monobasic, monohydrate | 1.80 |
| Deionized water, bailed | 1000.00 |
| TOTAL | 1019.80 |

The artificial saliva concentrate was diluted as follows:

| | |
|---|---|
| Concentrate | 1 part by weight |
| Deionized water, boiled | 9 parts by weight |
| TOTAL | 10 Parts by weight |

The pH of the diluted artificial saliva concentrate was adjusted to 7.0 with sodium phosphate, dibasic, $7H_2O$.

MTS Cyclic Compression /Tension Test:

The apparatus included a specially designed fixture having a 3" diameter Plexiglas upper plate and a 2" diameter Plexiglas lower plate, surrounded by a 4.5" diameter Plexiglas cylinder to form a reservoir. Special adapters were fabricated for mounting in the MTS instrument. Two milliliters of the dental adhesive sample were dispensed from a 5-ml disposable syringe and spread evenly onto the lower stage of the test fixture. The fixture reservoir was filled with artificial saliva so as to barely immerse the surface of the sample (about 180 ml). The upper stage of the fixture was brought into contact with the sample, leaving a starting position span of 0.04" above the lower plate. The instrument was cycled to travel up to a span of 0.06" and down to a span of 0.03" at a crosshead speed of 0.20 inch per minute and full-scale load of 20 to 50 lbs. The test was operated for 200 cycles, and the tension and compression forces were recorded. Formulations were run in triplicate and the averages were reported.

What is claimed is:

1. A process for preparing a toothpaste composition consisting essentially of agglomerating a water-soluble or water swellable polymer with water or an aqueous solution of a polymer and drying to form at least partially agglomerated particulates, stirring the particulate water-soluble or water-swellable polymer into a) humectant or a mixture of humectants, b) humectant vehicle, c) salts, colorants, and dentifrice actives, d) abrasive, e) surfactants, and f) flavors to obtain a complete dentifrice formulation.

2. The process of claim 1, wherein the agglomerated water-soluble or water-swellable polymer hydrates in polyhydric alcohols, water or water-containing solvents substantially faster than untreated water-soluble or water-swellable polymer, without formation of polymer lumps or significant dusting.

3. The process of claim 1, wherein the water-soluble or water-swellable polymer is a polysaccharide.

4. The process of claim 3, wherein the polysaccharide is at least one member selected from the group consisting of cellulose ethers (excluding MHPC alone), guar, guar derivatives, locust bean gum, psyllium, gum arabic, gum ghatti, gum karaya, gum tragacanth, carrageenan, konjac, agar, alginates, xanthan, scleroglucan, dextran, pectin, starch, starch derivatives, chitin chitosan, and processed euchemia seaweed (PES).

5. The process of claim 3, wherein the polysaccharide is at least one cellulose ether selected from the group consisting of hydroxyethyl cellulose (HEC), hydroxypropyl cellulose (HPC), water soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC) (when used in combination with other polymers), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC) and cationic hydrophobically modified hydroxyethyl cellulose (cationic HMHEC).

6. The process of claim 3, wherein the polysaccharide is at least one guar derivative selected from the group consisting of carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar) and hydrophobically modified cationic guar (HM cationic guar).

7. The process of claim 3, wherein the polysaccharide is selected from the group consisting of carboxymethyl cellulose, carrageenan, xanthan, guar, PES, starch, starch derivatives, pectin, and mixtures thereof.

8. The process of claim 3, wherein the polysaccharide is carboxymethyl cellulose.

9. The process of claim 3, wherein the polysaccharide is carrageenan.

10. The process of claim 3, wherein the polysaccharide is a mixture of carboxymethyl cellulose and carrageenan.

11. The process of claim 1, wherein the water-soluble or water-swellable synthetic polymer is homo- or copolymer comprising an acrylic acid or acrylic acid salt monomer, homo or copolymer comprising of ethylene oxide or propylene oxide, copolymer of poly(methyl vinyl ether/maleic anhydride), and polyvinylpyrrolidone.

12. The process of claim 1, wherein the water-soluble or water-swellable polymer is a mixture of polysaccharide and a synthetic polymer.

13. The process of claim 12, wherein the polysaccharide is selected from the group consisting of CMC, HEC, carrageenan, and xanthan gum.

14. The process of claim 13, wherein the synthetic polymer is selected from the group consisting of a homo- or copolymer comprising acrylic acid or acrylic acid salt monomer, and a homo- or copolymer comprising ethylene oxide or propylene oxide monomer.

15. The process of claim 1, wherein the oral care composition is a dentifrice or a dental adhesive.

16. The process of claim 15, wherein the oral care composition is a dentifrice composition and further comprises dental abrasive and humectant.

17. The process of claim 16, wherein the humectant is a polyhydric alcohol.

18. The process of claim 17, wherein the polyhydric alcohol is selected from the group consisting of glycerol, sorbitol, polyethylene glycol, propylene glycol, and mixtures thereof.

19. The process of claim 1, wherein the at least partially agglomerated particulate water-soluble or water-swellable polymer is prepared by spraying water or aqueous solution of the polymer onto particles of water-soluble or water-swellable polymer and drying the particles.

20. The process of claim 19, wherein the spraying of the water or aqueous solution of the polymer onto the particles takes place in a fluidized bed.

21. The process of claim 1, wherein the dentifrice further comprises ingredients selected from the group consisting of secondary thickener, flavors, herbs, sweeteners, preservatives, detergent, surfactants, antibacterial, coloring agents, opacifier, buffering agent, sequestering agents, film former, antiplaque agents, tartar control agents, vitamin, antimicrobial, breath freshener, teeth whitening agent and fluoride.

22. An oral care composition prepared by the process of claim 1.

23. The process of claim 21, wherein the dentifrice contains no polyhydric alcohols.

24. The process of claim 16, wherein the dentifrice is anhydrous.

25. The process of claim 15, wherein the dentifrice contains no humectants or organic solvents.

26. The process of claim 15, wherein the dental adhesive is in the form of a powder or paste.

27. The process of claim 26, wherein the paste comprises a polysaccharide, tackifier, secondary adhesive, vehicle, filler, flavor, color, wetting agent, extrusion aid, and humectant.

28. The process of claim 26, wherein the powder comprises a polysaccharide, secondary adhesive, tackifier, filler, flavor, and an anticaking agent.

* * * * *